United States Patent [19]

Kortright et al.

[11] Patent Number: 4,886,742
[45] Date of Patent: Dec. 12, 1989

[54] ENZYME IMMUNOASSAY FOR DETECTING HIV ANTIGENS IN HUMAN SERA

[75] Inventors: Kenneth H. Kortright, Cooper City; David E. Hofheinz, Homestead; Meryl A. Forman, Miami; Song Y. Lee, Plantation; Paulette E. Smariga, N. Miami; Candie S. Stoner, Hollywood, all of Fla.

[73] Assignee: Coulter Corporation, Hialeah, Fla.

[21] Appl. No.: 118,149

[22] Filed: Nov. 6, 1987

Related U.S. Application Data

[63] Continuation-in-part of Ser. No. 61,979, Jun. 15, 1987.

[51] Int. Cl.⁴ ................. G01N 33/577; G01N 33/569
[52] U.S. Cl. .................................... 435/5; 435/7; 435/70.21; 435/240.27; 435/172.2; 422/61; 436/510; 436/518; 436/531; 436/800; 436/805; 436/808; 436/809; 436/811; 436/825; 436/826; 530/387
[58] Field of Search ............. 435/5, 7, 240.27, 68, 435/172.2; 436/510, 518, 531, 800, 805, 808, 809, 811, 825, 826; 422/61; 530/387

[56] References Cited

U.S. PATENT DOCUMENTS 4,748,110  5/1988  Paul ........................................ 435/5
4,755,457  7/1988  Guroff et al. ......................... 435/5

FOREIGN PATENT DOCUMENTS 0173295  3/1986  European Pat. Off. ............. 435/5
0216191  4/1987  European Pat. Off. .

OTHER PUBLICATIONS

D. S. Healy, et al., Comparison of enzyme immunoassay and reverse transriptase assay for detection of HIV in culture supernates, J. Virol. Methods 17:237-245 (1987).
Kanki et al, "Serologic Identification and Characterization of a Macaque T-Lymphotropic Retrovirus Closely Related to HTLV-III", Science 228 (1985) 1199-1201.
Ferns et al, "Characterization of Monoclonal Antibodies Against the Human Immunodeficiency Virus (HIV) gag Products and Their Use in Monitoring HIV Isolate Variation", J. Gen. Virol, 68 (1987) 1543-1551.
Caruso et al, "Liquid competition radioimmunoassay for the detection and quantitation of the HIV p24", J. Virol. Meth., 17 (1987) 199-210.
Hattori et al, "Characterization of Three Monoclonal Antibodies (VAK3-5) That Identify p24, Core Protein of Human Immunodeficiency Virus, and Its Precursors", Jpn. J. Cancer Res. (Gann), 78 (1987) 235-241.
Ghrayeb et al, "Human T-Cell Lymphotropic Virus Type III (HTLV-III) Core Antigens: Synthesis in Escherichia coli and Immunoreactivity with Human Sera", DNA, 5 (1986) 93-99.
Higgins et al, "Detection and Differentiation by Sandwich Enzyme-Linked Immunosorbent Assay of Human T-Cell Lymphotropic Virus Type III/Lymphadenopathy-Associated Virus- and Acquired Immunodeficiency Syndrome-Associated Retroviruslike Clinical Isolates", J. Clin. Microbiol., 24 (1986) 424-430.
Evans et al, "Human Monoclonal Antibody Directed Against gag Gene Products of the Human Immunodeficiency Virus", J. Immunol., 140 (1988) 941-943.
Cohen et al, "Enumeration of CR1 complement receptors of erythrocytes using a new method for detecting low density cell surface antigens by flow cytometry", J. Immunol. Meth., 99 (1987) 53-58.
Kanner et al, "Human Retroviral env and gag Polypeptides: Serologic Assays to Measure Infection", J. Immunol, 137 (1986) 674-678.

Primary Examiner—Christine M. Nucker
Attorney, Agent, or Firm—Myron C. Cass

[57] ABSTRACT

A solid-phase immunoassay is provided for determination of HIV antigens in human physiological fluid. The immunoassay is characterized by the coating of a solid substrate with a unique monoclonal antibody which recognizes a common antigenic determinant of a group of HIV core antigens and no HIV envelope antigens of HIV. The test sample preferably also is subjected to a lysing reagent prior to the incubation for uniformly dispersing antigens which may be present in the test sample.

12 Claims, 3 Drawing Sheets

ENZYME IMMUNOASSAY FOR DETECTING HIV ANTIGENS IN HUMAN SERA

RELATED CASE

This is a continuation-in-part application of pending application, Ser. No. 061,979 filed June 15, 1987, titled SIMULTANEOUS ENZYME IMMUNOASSAY FOR DETECTING ANTIGEN AND/OR ANTIBODY IN HUMANS and is incorporated by reference. The identified patent applications enjoy common ownership.

FIELD OF INVENTION

This invention provides an improved immunoassay for detecting HIV antigens in a human physiological fluid test sample which may have circulating antigens.

This invention in a preferred embodiment provides a unique enzyme immunoassay which can be performed for detecting HIV virus, HIV virus fragments or HIV infected cells. This immunoassay provides a test result of positive or negative HIV antigen, as the case may be, with a greater degree of accuracy or sensitivity, consistency and in a shorter period of time than has been realized heretofore in an HIV antigen assay. The assay embodying the invention uses solid-phase assay methodology in which a monoclonal antibody specific to certain HIV core antigens is coated on the solid surface.

BACKGROUND OF THE INVENTION

HTLV III infection, now referred to as HIV infection, commonly results in AIDS (Acquired Immune Deficiency Syndrome). Reported increasing numbers of AIDS patients in the United States has caused the disease to be recognized as approaching epidemic proportions with no known cure or vaccine. The occurrence of AIDS has been increasing primarily in Europe and African countries of the world as the disease is transmitted through sexual activity, drug abuse, contaminated organs in transplantation procedures and by blood transfusions. Other strains of the HIV such as HTLV IV are developing through mutation of this virus.

Separate tests for the presence of HIV antibody or HIV antigen have been developed by investigators, including scientists at the National Institute of Health (NIH). Assays for detecting HIV antibody in plasma and serum have received clinical approval for commercialization. Assays for detecting HIV antigen are known for research use but to our knowledge none has received clinical approval for commercialization. These tests separately and independently analyze the plasma, serum or blood cell culture supernatant of screened individuals for HIV antigen or human anti-HIV antibody content which binds the HIV antigen, see Anti-HIV Testing: Screening and Confirmation Tests, Medical Laboratory Products, April 1987, p. 16–18, for a recent review article comparing several such separate tests.

Human antibody develops in 70–80% of the people exposed to HIV through sexual intercouse, blood transfusions, contaminated organs through transplantation or contaminated needles by drug abusers. The remaining 20–30% of exposed individuals who do not develop antibodies against the invading virus for a period of up to six months can remain undetected carriers in society. Therefore, if one is to effectively screen blood and organ donors, individuals, or blood products for containing the spread of AIDS, it is essential that the screening immunoassay be able to detect not only HIV antibody but also the HIV virus itself and/or infected cells carrying the virus.

Heretofore difficulty has been encountered with false-positive results which may occur due to nonspecific antibodies or to antibodies directed against antigens in supporting cell cultures used to obtain supernatants containing viral particles in sufficient quantity as is generally necessary to overcome the less than desirable sensitivity of prior tests.

The assay embodying the invention successfully tests for the virus and virus infected cells. The assay can be performed in a single vessel such as a microtiter plate well. Preferably, the patient's test sample comprises human plasma, i.e., whole blood from which all cells have been removed initially, or serum, i.e., plasma from which all clotting factors have been removed. The assay provides a result of "positive" or "negative" as the case may be, by enzyme immunoassay (EIA). The suitability of the use of the assay of this invention to identify AIDS infected patients is significantly greater than has been realized heretofore where an immunoassay tracks only antibodies to HIV in a physiological sample such as peripheral blood. The test result is achieved in approximately four hours.

Lysing of viral concentrates to release viral proteins prior to using electrophoresis to spread viral proteins, i.e., antigens, on polyacrylamide gel is known with respect to a Western blot technique for confirming the presence of only anti-HIV antibodies, not antigens, and is thus of no practical utility during that period of time prior to when no antibodies are present even though the patient has been infected with HIV. Similarly, the use of an HIV viral lysate as a solid phase protein adhered to a solid phase support, such as a microtiter plate formed of polystyrene, is known with respect to an ELISA technique for screening for anti-HIV antibodies, not antigens, during the period after HIV infection when no antibodies are present. However, it has not been recognized that the lysing of HIV in a patient's blood sample in contact with a unique monoclonal antibody coated solid phase in the presence of a mammalian biotinylated anti-HIV antibody can provide for the relatively rapid, sensitive quantitative measurement of HIV antigens in a single test sample as realized by this invention.

SUMMARY OF THE INVENTION

An enzyme immunoassay is provided for testing HIV antigen in a human physiological fluid test sample such as plasma or serum or cell culture supernatant. In a preferred embodiment of the invention, the immunoassay is used to test a single sample for HIV antigens wherein the methodology used is that of solid-phase assay, e.g., enzyme-linked immunosorbent assay (ELISA) that uses microtiter strips, polystyrene beads, or ferrous beads, for example, as support media. In a particularly preferred embodiment, the test sample or specimen of predetermined volume, such as 200 microliters (uL), is introduced into a well of a microtiter plate which has been coated with a unique monoclonal antibody which recognizes the same epitope of a group of core antigens. A cell lysing reagent is introduced and the mixture incubated for a suitable period of time at 37° C. A quantity of preferably human anti-HIV antibody biotin complex reagent is added and incubated for a suitable period of time. The sample is then subjected to incubation procedures which utilize selected developing reagents. The entire assay is completed in approximately four hours.

The immunoassay of this invention differs from that described in the parent application in three major respects. The use of the so-called "Spike" is eliminated. The preferably human anti-HIV antibody biotin complex has a particular formulation. The solid phase is coated with a unique monoclonal antibody identified as the KC-57 monoclonal antibody.

PREFERRED EMBODIMENT OF THE PARENT APPLICATION

Figure 1:
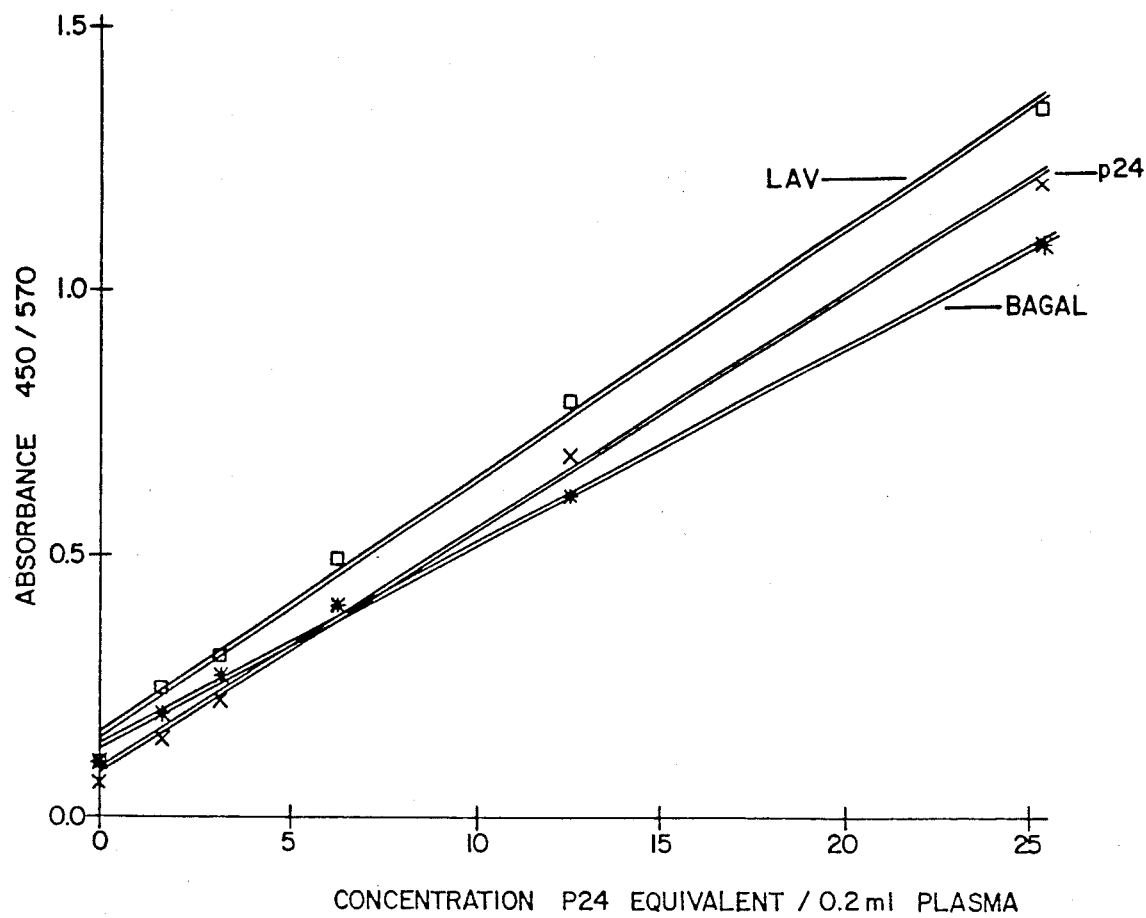
FIG. 1 is a graph of representative standard curves developed from assays using normal human serum spiked with culture media taken from human lymphocyte cultures infected with two isolates of HIV and purified p24 antigen from a LAV infected human T cell line.

In the preferred embodiment of the parent application there is provided an assay of a single sample for simultaneous detection of HIV antigen and/or HIV antibody in a human physiologial test sample, such as plasma or serum. Microwells, such as of a microtiter plate having microwell strips, are coated with HIV antibody obtained from sera which exhibit high titers of anti-HIV antibody. The solid-phase support media, i.e., the microtiter plate is prepared for the assay by coating the wells with purified anti-HIV antibody derived from a high titer mammalian serum or plasma source such as from a human, goat or other species.

Test sample is added to one coated microwell, or preferably several coated microwells, since duplicate tests are preferred. Control wells are provided for normal, i.e., antigen and antibody negative, physiological fluid, e.g., normal human plasma or serum. An antigen positive control well preferably is also used. A known amount of HIV antigen, i.e. the "Spike" is added to each sample microwell and each control well or wells and the so-combined sample and added antigen subjected to a lyse buffer to assure disruption of virus present in the test sample into its component parts. After a simple incubation at body temperature the microtiter plate is washed to remove material which might interfere with the signal producing system and the captured antigen is next allowed to react with anti-HIV antibody which has been conjugated with biotin. Following a subsequent incubation with streptavidin-peroxidase reagent, color development of bound enzyme is revealed using an appropriate substrate. Resultant optical densities are proportional to the relative amount of HIV antigen, and/or anti-HIV antibody, occurring in the test sample and antigen positive control or the absence thereof in the test sample and controls.

As is customary, the antibody coated solid-phase support and generally all of the reagents necessary for carrying out an assay are provided in kit form. In the practice of the preferred embodiment of this invention such a kit comprises:

A 96 well polystyrene microtiter plate with the wells coated with anti-HIV antibody;

A supply of plate covers;
Lyse Buffer;
Antigen Reagent "Spike";
Antigen Diluent;
Anti-HIV Antibody-Biotin Reagent;
Biotin Reagent Diluent;
Streptaviden-Horseradish Peroxidase (HRPO) Conjugate;
3,3',5,5'Tetramethylbenzidien (TMB) reagent;
TMB Substrate Buffer;
Normal Human Plasma Control;
Normal Human Serum Control;
Antigen Positive Control (50 pg antigen per 20 uL)
10X Wash Buffer;
Hydrogen Peroxide Solution; and
Stopping Solution.

GLOSSARY OF REAGENTS

The reagents are generally required to be prepared in advance so that they will be available at the appropriate steps in carrying out the exemplary preferred immunoassay procedure. These are as follows:

Lyse Buffer:

| | |
|---|---|
| Peroxide-free octylphenolpoly (ethyleneglycolether) e.g. Triton X-100, Boehringer Mannheim Biochemicals Polyoxyethylenesorbiton monolaurate | 5% |
| e.g. Tween 20, Sigma Chemical Co. | 2% |
| Sodium Ethylmercurithiosalicylate e.g. Thimersol, Sigma Chemical Co. | 0.05% |
| Dye, FDC Blue No. 1 | 0.9 mg/ml |
| Distilled water | Q.S.1 L |

Antigen Reagent:
HIV antigen content sufficient when diluted with antigen diluent to provide Spike of 50 picograms of HIV antigen per 20 uL of diluted reagent. The concentration of antigen in the Spike may be determined on the basis of P24 equivalent by use of a DuPont P24 Radioimmunoassay (RIA).

Antigen Diluent:

| | |
|---|---|
| Protease-Free Bovine Serum Albumin (BSA) in Phosphate Buffered Saline (PBS) | 1.0% |
| Sodium azide | 0.1% |
| Dye, FDC Red No. 3 | 0.5 mg/ml |

Anti-HIV Antibody-Biotin Reagent:
Human anti-HIV Antibody-Biotin Conjugate (preferably lyophilized)
Biotin Reagent Diluent: For 1 L

| | |
|---|---|
| Triton X-100 | 0.5% |
| Normal Human Serum (heat inactivated) | 0.5% |
| Tween | 0.2% |
| Thimersol | 0.5% |
| 10X PBS (10 mM phosphate, 145 mM NaCl pH 7.2) | 100. ml |
| Distilled Water | Q.S.1L |

Streptavidin-HRPO Conjugate:
Calbiochem-Behring Corp.
TMB Reagent:

| | |
|---|---|
| TMB | 1.0 g |
| DMSO (dimethyl sulfoxide) | Q.S. 100.0 ml |

TMB Dilution Buffer:

| | |
|---|---|
| Na$_2$HPO$_4$7H$_2$O | 24.13 g |
| Citric acid monohydrate | 11.38 g |
| Chloracetamide | 1.00 g |
| Distilled water | Q.S. 1L |
| pH adjusted to 4.4 | |

Stopping Solution:

| | | |
|---|---|---|
| 18M concentrated H$_2$SO$_4$ | 100.0 | ml |
| Distilled water | 800.00 | ml |

Hydrogen Peroxide Solution:
30% H$_2$O$_2$
10X Wash Buffer (Dilute 1 to 10):

| | | |
|---|---|---|
| Tween 20 | 10.0 | ml |
| 10X PBS | 0.99 | L |
| 1% Chloracetamide | 10.0 | g |

Depending upon the nature of the reagents, as well as the protocol, it will be appreciated by those skilled in the immunoassay art that the concentration of individual reagents can be varied widely once it is appreciated that a significant aspect of this invention resides in the step of adding a Spike consisting of a known amount of antigen of the single binding pair being assayed.

IMMUNOASSAY PROCEDURE

The immunoassay embodying the invention of the parent application preferably is performed in a familiar microtiter plate well. In the preferred embodiment, a 200 microliter (uL) patient sample is tested. The patient sample may comprise human plasma derived from whole blood from which the cells have been removed by centrifugation, for instance, serum, or cultured cells. The test sample of 200 uL is introduced into the well of the microtiter plate which has been coated with a heat inactivated purified anti-HIV antibody.

The purified anti-HIV antibody is derived from a high titer serum or plasma source. Such a source can be a human one. To coat a well, the mammalian antibody, e.g., human anti-HIV antibody is diluted to 2.5 micrograms per mililiter in so-called "plating buffer". The plating buffer is comprised of 250 mM of potassium phosphate at pH 6.0. 250 uL of diluted antibody is pipetted into the well and stored at 4° C. for approximately sixteen hours. The well is then drained and washed three times in a phosphate buffered saline (PBS) wash solution. The well is then blocked for one hour at room temperature with 330 uL of a blocking reagent comprising 1% bovine serum albumin (BSA) (Protease free), 5% Sucrose plus 1% sodium ethylmercurithiosalicylate in 1 times PBS filtered through a 0.2 um filter. The well is stored for up to six hours with the blocking solution at 4° C. until dried. The well is then drained, speed vacuum dried and stored at 4° C. in a bag with dryite desiccant bag.

Although the coating procedure has been described for a single well, conventional microtiter plates are available with a plurality of wells. Also available is equipment for coating a plurality of wells. Thus, the immunoassay embodying the invention can be performed utilizing such available equipment with a plurality of wells.

To the 200 uL test sample in the well is added 20 uL of Lyse Buffer for lysing the infected cells and 20 uL of Human Antigen Working Solution which is the antigen reagent diluted with antigen diluent to the preselected 50 pg antigen per 20 uL. The well is then covered and mixing of ingredients in a suitable shaker is performed for one minute. The mixed materials are then incubated for one hour at 37° C.

After incubation, the well is aspirated and washed three times in a conventional manner with wash buffer. The anti-HIV antibody-biotin which is preferably in a lyophilized state is reconstituted and diluted to a 5% solution with biotin reagent diluent and 200 uL added to the well and the plate incubated at 37° C. for one hour.

After incubation, the well is aspirated and washed three times using the Wash Buffer reagent. The 200 uL of the streptavidin-peroxidase conjugate is added to the well, covered and incubated for thirty minutes at 37° C. After incubation, the well is aspirated and washed three times with the Wash Buffer. Then, 200 uL of TMB Substrate Solution is introduced to the well, covered and incubated for thirty minutes at room temperature.

Then, 50 uL of 2 Molar sulfuric acid is added to the well to stop the reaction. The optical density of the solution in the well is then read on a microtiter plate reader at a wavelength of 450 nanometers using 570 nanometers as a reference where dual wavelength capability is available. If dual wavelength capability is not utilized, the plate can be read at both wavelengths and the 450 nanometer readings corrected by subtracting the 570 nanometer readings.

The immunoassay embodying the invention provides for a quantitated patient sample including a predetermined quantity of a Spike of inactivated HIV viral antigen, which is detectable at a designated picogram sensitivity, to be introduced into an antibody coated microtiter well. Various conventional incubations follow, using prescribed human developing agents, such as, biotin covalently coupled to a mammalian specie derived anti-HIV antibody such as derived from a human. The coupling is followed by a step of forming a biotin-avidin conjugated peroxidase complex after which the TMB substrate is added to provide colormetric visualization of the reaction. A particularly favorable degree of sensitivity for the test was noted when the HIV antibody biotin conjugate employed a long chain biotin. The concentration of Spike antigen and the antigen in the patient sample placed in the well which binds to the capture antibody coated walls of the well is then recognized by the anti-HIV antibody which is biotinylated and the complex then reacted with the avidin peroxidase and TMB substrate for visualization of the reaction. After stopping the reaction, the EIA readings can be taken to compare against control directed readings.

The reading obtained from the patient test sample is compared to the control readings such as those obtained from normal human plasma free of HIV antigen, anti-HIV antibody, or non-infectious virus subjected to the immunoassay procedure. We have established the reference point for a test result using a patient sample as an increase or decrease of about 30%. Thus, if an optical density reading decreases more than 30% from the OD of the Spike, the determination is antibody positive. If the reading increases more than about 30%, the the determination is antigen positive.

While an ELISA using a combination of a ligand and receptor, i.e., biotin-avidin protocol for providing a detectible signal for the immunological reactions has been described in the preferred methodology, it will be appreciated that numerous other methodologies may be employed for visualizing the resultant immunological reactions. In this regard, other labels or markers may be employed for visualizing the resultant immunological reactions, such as radionuclides, other enzymes, fluorescers, chemiluminescers, enzyme substrates, particles, e.g., magnetic particles, combinations of ligands and receptors other than biotin and avidin.

A series of tests were conducted in accordance with the above described improved ELISA protocol for simultaneous determination in a single test well of both HIV antigen and/or anti-HIV antibody. The tests were conducted on plasma and serum derived from blood samples obtained at five medical institutes from patients suspected of being exposed to HIV, diagnosed as having an ARC or suspected of having, or diagnosed as having AIDS. In the test series, three 96 well microtiter plates were used to perform 99 assays.

With respect to microtiter plate 1, there were 32 tests run and the 50 pg per 20 ul spike used to establish the base line optical density exhibited an optical density (OD) that equals $0.894 \pm 0.061$. Using an arbitrary guideline of 30% deviation in optical density below and above 0.894, it was established for purposes of the assay that OD of <0.626 equals anti-HIV antibody positive and OD of >1.16 equals HIV antigen positive.

Similarly with respect to plate 2, 34 tests were run and the 50 pg Spike had an OD of $0.715 \pm 0.56$. An OD reading of <0.500 was considered to be anti-HIV antibody positive and OD of >0.93 was considered to be HIV antigen positive.

By the same rationale, with respect to plate 3, 33 tests were run and the 50 pg Spike had an OD of $0.655 \pm 0.59$ whereby an OD of <0.459 was considered to be anti-HIV antibody positive and an OD of >0.852 was considered to be HIV antigen postive.

The samples were all subjected to a screening test by an ELISA technique other than that of the present invention and were also subjected to a confirmation test using a Western blot technique for analysis and identification of HIV proteins P24 and P120 before assigning a "score" of positive or negative to the sample. Of the 99 samples, 70 or 70.7% were determined to be positive to either HIV antigen or anti-HIV antibody and 29 or 29.3% determined to be negative to either HIV antigen or anti-HIV antibody. Of the 70 samples found to be positive, 6 samples or about 6.1% were found to be both HIV antigen and anti-HIV antibody positive. However, the particular significance of the immunoassay comprising the present invention will be appreciated from the fact that 17 of the samples determined to be "positive" were found to only be positive with respect to HIV antigen.

It is a significant advance in immunoassay to have the ability to simultaneously screen a physiological fluid sample in a single test vessel for both antigen and antibody of a single binding pair. In the preferred embodiment of the invention, this enables simultaneous screening, by use of a single test well, a test sample of plasma or serum from donated blood for both anti-HIV antibody and HIV antigen or more importantly the presence of only HIV antigen. The critical need to identify donated blood containing only HIV antigen during that period of time between a person being infected with HIV and when antibodies to the HIV are raised or raised to a sufficient level to be detected by a screening test, need hardly be emphasized.

The test data compiled as a result of the Western blot confirmation tests performed appears to indicate that about 10% of the tests performed by the method of the present invention are subject to a false positive result and about 15% are subject to a false negative determination. It will be appreciated that the percentage of false results may be attributable to factors which were not determined, such as human error in conducting the test or reading the result. Thus, the percentage of apparent false results is not a true reflection of the efficacy of the exemplary test run described herein.

PREFERRED EMBODIMENT OF THIS INVENTION

This invention utilizes the individual procedures, reagents and apparatus to a substantial degree described in the parent application. However, there are certain reagents used and not used which represent important departures from the assay protocol of the parent application and which contribute to realizing the novel immunoassay for detecting HIV antigens in a patient embodying this invention.

The solid-phase support media is a microtiter plate prepared for the assay by coating the wells with a novel monoclonal antibody which recognizes a common epitope of certain core antigens and no envelope HIV antigens in a human physiological test sample. This monoclonal antibody was produced from a hybridoma or cell line developed at the laboratories of the common assignee by co-inventors common with those of this assay invention. The monoclonal antibody is identified as the KC-57 monoclonal antibody which recognizes an epitope common to the HIV antigens, P55, P24 and partial breakdown products P39 and P33. The KC-57 antibody does not bind the P18 core antigen or any other HIV associated antigens.

STATEMENT OF DEPOSIT

A cell line which produces the KC-57 monoclonal antibody corresponding to that used in this invention has been deposited in the American Type Culture Collection, 12301 Parklawn Drive, Rockville, Md. 20852 on Nov. 6, 1987, concurrently with the filing of this application. The cell line was assigned A.T.C.C. No. HB9585.

Coating of one or more micrtiter wells with the KC-57 monoclonal antibody is performed in substantially the same manner as described in the parent application. The KC-57 antibody is diluted to 2.5 micrograms per milliliter in the so-called "plating buffer". 250 microliters of diluted monoclonal antibody is pipetted into the well, stored, washed, blocked, dried, speed drained and stored again as herein described. A plurality of wells can be coated using commercially available automated pipetting apparatus.

A 200 microliter patient sample is tested, the sample being human serum or plasma derived from whole blood serum or culture cells. The 200 microliter sample is pipetted into a well and 20 ul of Lyse Buffer for lysing infected cells is added. The well is covered and then incubated for one hour at 37° C.

After incubation, the well is aspirated and washed three time in a conventional manner with wash buffer. 200 ul of Anti-HIV Antibody-Biotin Complex reagent, preferably lyophilized, is added in a reconstituted state. The Anti-HIV antibody preferably is derived from a human source, i.e., a high titer serum or plasma source. This reagent is reconstituted to a predetermined volume so that 200 ul of the reconstituted reagent can be introduced to a well. The plate is incubated for one hour at 37° C.

Thereafter, the well is aspirated and washed three times using a Wash Buffer reagent. The procedure of adding streptavidinperoxidase conjugate, incubation and adding 200 ul of the TMB Substrate Solution is as described in the parent application. Then, 50 ul of Molar Sulfuric Acid is added to a well to stop the reaction and the optical density of the solution is then read on a microtiter plate reader at a wavelength of 450 nanometers using 570 nanometers as a reference where dual wavelength capability is available. If dual wavelength capability is not uitlized, the plate can be read at both wavelengths and the 450 nanometer readings corrected by subtracting the 570 nanometer readings.

The EIA readings taken can be compared against control directed readings, such as those obtained from normal human plasma or serum free of HIV antigen in a KC-57 monoclonal antibody coated well acting as a negative control or those obtained from such a coated well into which 50 ul of a virus antigen reagent was introduced. The latter procedure would provide a positive control. Preferably, the assay embodying the invention would employ a pair of positive control wells. 200 ul of patient sample would be used in each of the above control well procedures.

As pointed out in the parent application, an ELISA immunoassay is not the only one applicable to this invention. Thus, other methodologies as enumerated herein are considered to be applicable.

TABLE 1

SUMMARY OF HIV ANTIGEN ASSAY RESULTS

| HIV NEGATIVE | # Tested | Initial False Positive | Repeatable False Positive |
|---|---|---|---|
| Normal | 245 | 3 | 0 |
| Rheumatoid Factor | 12 | 3 | 0 |
| Bilirubin | 15 | 0 | 0 |
| Chlamydia | 17 | 0 | 0 |
| Toxoplasmosis | 11 | 0 | 0 |
| HSV | 16 | 0 | 0 |
| Legionaires | 6 | 0 | 0 |
| EBV | 17 | 2 | 0 |
| CMV | 16 | 0 | 0 |
| Hepatitis | 4 | 0 | 0 |
| Mycoplasma | 1 | 0 | 0 |
| Subtotal | 360 | 8 | 0 |
| HIV POSITIVE | # Tested | Antigen Positive | % Positive |
| Diagnosed AIDS* | 61 | 27 | 44 |
| Blood Bank | 37 | 6 | 16 |
| Subtotal | 98 | 33 | 34 |

*Some samples from patients on AZT therapy.

Referring to Table 1, normal and abnormal HIV negative serum samples tested are listed and the number of samples tested is noted. The total number of samples tested was 360 of which Initial False Positive values were seen to be eight in number. Repeated tests of the eight samples indicated they were truly negative. Although 25% of the 12 rheumatoid factor containing sera were positive in this assay initially, they were not repeatable. It is believed that contaminating material in these sera may have created a false impression of a high incidence of initial positives.

With respect to the HIV POSITIVE data displayed, sera from 98 humans known to be serologically positive by Western Blot analysis, both asymptomatic and diagnosed AIDS patients, were tested. The percent positive determinations in each category of sera tested is listed. 44% of the diagnosed AIDS samples were positive for circulating p24 antigen. In Deborah A. Paul, et al, J. Med Virol, 22: 357: 363 (1987), 69% of diagnosed AIDS patients were found to have circulating HIV antigen. The difference between these two determinations may be attributed to the AZT therapy ("zidovudine", formerly known as azidothymidine), which is believed to account for rapid decline in the circulating HIV antigen levels. The 16% of asymptomatic individuals found to be positive correlates well with the 19% determination in Deborah A. Paul, supra.

TABLE 2

HIV ANTIGEN ASSAY - p24 SPIKED SAMPLE RESULTS

| p24 Antigen Positive Mass/200 ul | Number Performed | Number Positive | Calculated Recovery (%) |
|---|---|---|---|
| 25 pg | 169 | 169 | 100% |
| 6.25 pg | 165 | 165 | 100% |
| 1.56 pg | 162 | 141 | 87% |
| 0 pg | 156 | 0 | 0 |

Table 2 reflects data developed to show the accuracy of the assay embodying the invention. Normal human serum and normal human serum to which the p24 core antigen was added (called "spiked") were assayed. The levels of p24 spiked are itemized for each category of test conducted. At the 25 picogram (pg) and 6.25 pg per 200 microliters spiked level, 100% tested positive. At the 1.56 pg level, 87% tested positive. Normal human serum did not test positive in 156 assays performed.

TABLE 3

KC-57 HIV ANTIGEN CAPTURE ELISA

| HIV ISOLATE | REGION ISOLATED | RESULTS |
|---|---|---|
| LAV | France | + |
| BAGAL | New York City | + |
| 1265 D13 | Atlanta | + |
| Z34 | Zaire | + |
| SDR | San Francisco | + |
| 2153 D16 | New York City | + |
| 121886-1 | Bethesda | + |
| 1272 D21 | Chicago | + |

Table 3 demonstrates that the HIV antigen assay utilizing the KC-57 monoclonal antibody as a capture phase and human anti-HIV antibody as the detector phase identified all strains listed as being positive for HIV antigen content.

TABLE 4

SPECIFICITY OF KC-57 MONOCLONAL ANTIBODY

| Infectious Agent | # Tested | # Positive |
|---|---|---|
| EBV | 2 | 0 |
| HTLV I | 2 | 0 |
| HTLV II | 2 | 0 |
| HSV I | 2 | 0 |
| HSV II | 2 | 0 |
| CMV | 2 | 0 |
| Chlamydia | 2 | 0 |

The above table demonstrates the reactively of KC-57 antibody against other infectious agents when run in the HIV Antigen Assay. No reactivity is seen with any of these agents.

Referring to FIG. 1, this graph demonstrates representative standard curves developed from assays using normal human sera spiked with culture media taken from human lymphocyte cultures infected with two isolates of HIV, BAGAL and LAV, and purified p24 antigen from a LAV infected human T cell line. p24 antigen concentrations were established using the Dupont p24 RIA. Sensitivity for each preparation is shown to be less than 10 pg/ml.

Figure 2:
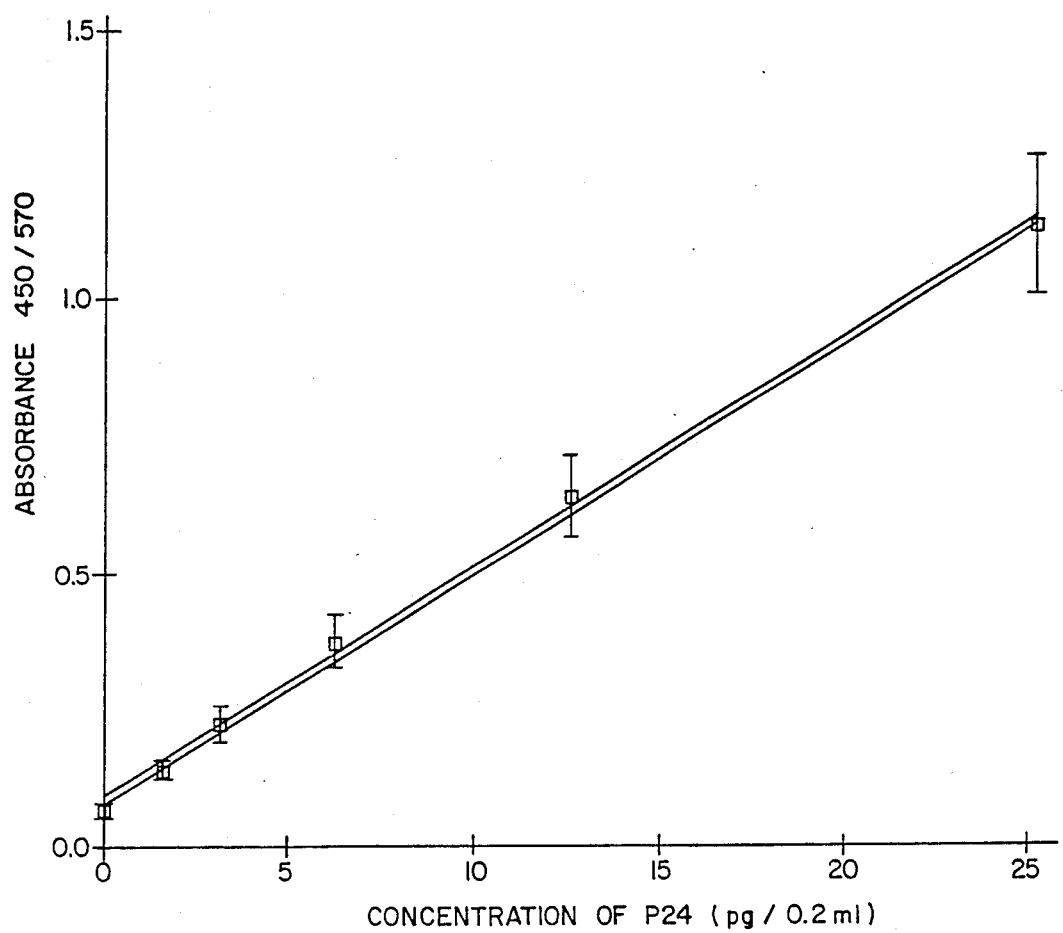
FIG. 2 is a graph of standard curves developed from assays when p24 antigen was spiked into normal human plasma.

Referring to FIG. 2, this graph demonstrates the sensitivity achieved with the assay analyzing p24 antigen spiked into normal human plasma. This data was collected by six individual assays run on separate days. A positive value, twice the background absorbance was obtained at 1.2 pg/well or 6 pg/ml. Interassay variation ranged from 11–26 percent.

Figure 3:
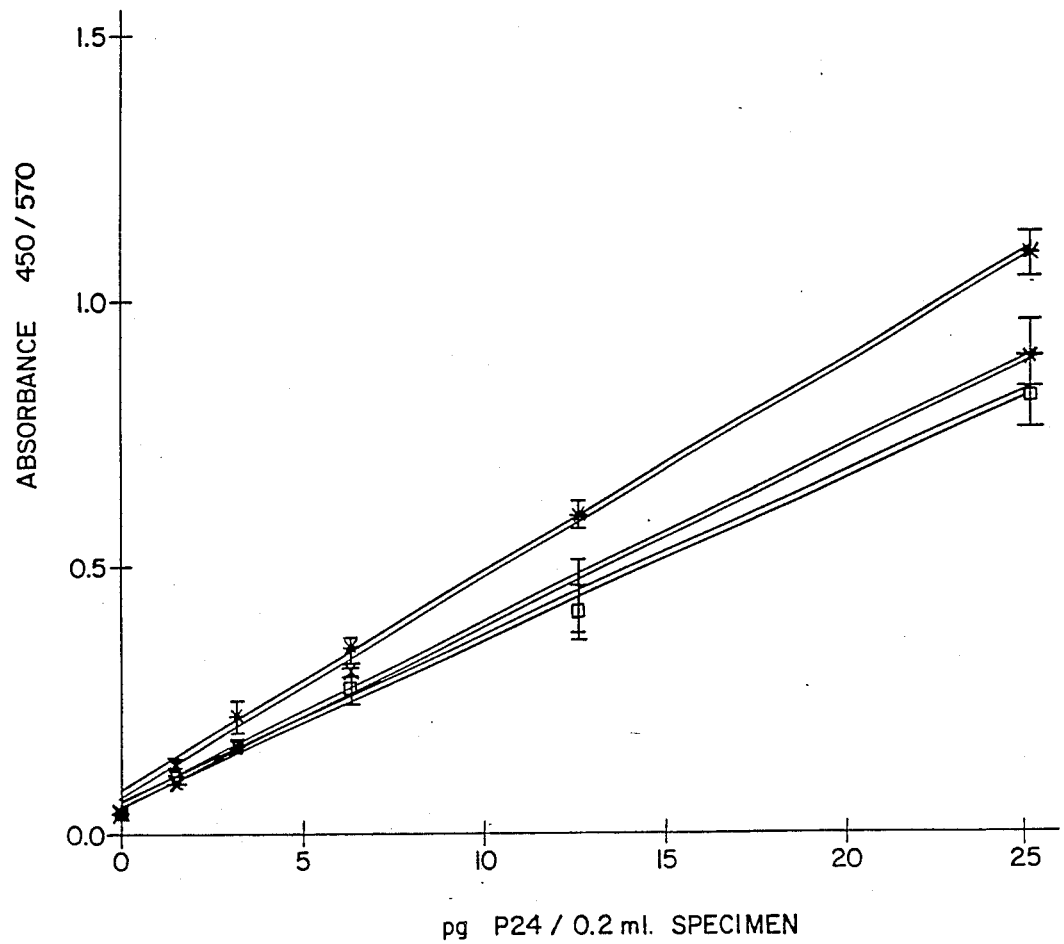
FIG. 3 is a graph of standard curves developed from assays when p24 antigen was spiked into culture medium, normal human plasma or serum.

Referring to FIG. 3, this graph demonstrates the sensitivity achieved analysing p24 antigen spiked culture medium, normal human plasma, or serum. Linear regression standard curves obtained through the analyses of these viral preparations, demonstrate no significant difference between sera and plasma with culture media demonstrating slightly higher background and specific absorbance.

GLOSSARY OF REAGENT CHANGES

Antigen Reagent

HIV antigen content sufficient when diluted with an appropriate diluent which will provide an Antigen Reagent concentration of 25 pg p24 per 50 ul. Addition of 50 ul Antigen Reagent to 0.2 ml normal human plasma, human serum or culture media will provide a positive control with an approximate absorbance value (450/570) of $1.00 \pm 0.250$.

Biotin Reagent (4 X Concentrate) 125 ml

| | |
|---|---|
| Triton X-100 | 2.0% |
| Tween 20 | 0.8% |
| Normal Human Serum (Heat Inactivated) | 2.0% |
| Non-fat Dry Milk | 20.0% |
| Thimerosol | 0.25 g |
| 10 × PBS (100 mM, 1.45 m NaCl) | 50.0 ml |
| Anti-HIV antibody Biotin complex | 0.3125 mg |
| Distilled Water | QS 125.0 ml |

TMB Diluent Buffer

| | |
|---|---|
| $Na_2HPO_4 7H_2O$ | 24.13 g |
| Citric Acid Monohydrate | 11.38 g |
| Chloracetamide | 1.0 g |
| Distilled $H_2O$ | QS 1L |
| Adjust pH to 4.4 | |
| Add 0.15 ml 30% $H_2O_2$ | |

To demonstrate the consistency or repeatability of the HIV antigen assay of the invention, a series of six assays were conducted over a period of three days. Zero levels or negative controls and 25 picograms of P24 core antigen were the samples assayed. The average and standard deviation ($\bar{X} \pm S.D.$) of the negative control was $0.069 \pm 0.013$ with an 18% intra-assay variability. Inter-assay variability was 20% with an average and standard deviation ($\bar{x} \pm S.D.$) of $0.069 \pm 0.017$. The 25 picogram level demonstrated on intra-assay variability of 1% with an average and standard deviation ($\bar{x} \pm S.D.$) of $1.149 \pm 0.012$. The inter-assay variability was 11% with an average and standard deviation ($\bar{X} \pm S.D.$) $1.149 \pm 0.128$.

The immunoassay embodying the invention achieves important advantages. The stability of the enzyme color reactionn of a test is up to four (4) hours. This means that there will be no concern about checking a color determination after a test is completed since replication is possible for up to four hours thereafter. For a 96 well microtiter plate provided in a kit with the requisite reagents for performing the assay and using five (5) wells as control wells, 90-91 tests can be conducted within an approximate four hour period since the wells will already be coated with KC-57 monoclonal antibody. Applicants are not aware of any HIV antigen assay capable of this productivity in so short a period of time. The sensitivity and replication of results achieved with this assay is entirely without precedent in the art as known to applicants.

We claim:

1. An immunoassay for detecting HIV antigens in a human physiological fluid test sample containing cells and which sample may have circulating antigen, said assay comprising:
   (a) introducing into contact with a solid surface to which is bound a known quantity of a monoclonal antibody capable of binding to a common epitope of the HIV p55, p24, p39 and p33 core antigens and without binding the HIV p18 core antigen and HIV envelope antigens, a predetermined volume of the test sample;
   (b) incubating said test sample in contact with said surface to form resultant antigen-antibody complexes; and
   (c) incubating the resultant complexes and subjecting same to a labelled human anti-HIV antibody conjugate which is capable of yielding a quantitatively measurable signal correlated to the signal for a normal negative test sample to indicate either antigen positive or negative for the test sample with picogram sensitivity of at least approximately 7.8 picograms per milliliter of test sample within a period of approximately four hours from the time of commencement of the immunoassay.

2. The immunoassay of claim 1 and including the step of introducing to the test sample and said surface of step (a) of a lysing reagent for uniformly releasing antigens available from said cells during incubation.

3. The immunoassay of claim 1 in which said antibody of step (c) is labelled with an enzyme which is capable of producing the said signal when contacted with an enzyme substrate.

4. The immunoassay of claim 1 in which said monoclonal antibody is the KC57 monoclonal antibody produced from a hybridoma cell line having the identifying characteristics of the cell line samples on deposit with the American Type Culture Collection, Rockville, Md., and assigned A.T.C.C. deposit No. HB 9585 producing mouse IgG1 monoclonal antibody to the KC-57 antigen.

5. The immunoassay of claim 1 in which the labelled human anti-HIV antibody conjugate of step (c) is a glycoprotein bound antibody conjugate labelled with an enzyme capable of producing a color detection signal when contacted with an enzyme substrate.

6. The immunoassay of claim 5 in which said conjugate is a biotinylated antibody.

7. A kit for use in performing an immunoassay for detecting HIV antigens in a physiological fluid test sample comprising in combination:
   (a) a solid surface to which is bound a known quantity of the KC-57 monoclonal antibody capable of binding with a common epitope of the HIV p55, p24, p39 and p33 core antigens and which does not specifically bind to the HIV p18 core antigen and HIV envelope antigens;

(b) a container containing an amount of a labelled human anti-HIV antibody conjugate for providing a useful detectible signal for a test sample;

(c) a container containing an amount of a lysing agent for uniformly releasing viral antigens which may be present in cells in a test sample; and (d) containers of incubating and washing reagents necessary for visualizing immunological reactions resulting from use of the kit in performing the immunoassay said combination selected quantitatively to obtaining such visual immunological reactions at picogram sensitivity within a period of approximately four or less hours from the time of commencement of said immunoassay.

8. The kit described in claim 7 in which said monoclonal antibody is the KC-57 monoclonal antibody produced from a hybridoma cell line which has the identifying characteristics of the hybridoma cell line samples on deposit with the American Type Culture Collection, Rockville, Md. and assigneed A.T.C.C. deposit No. HB 9585.

9. An immunoassay for detectinng HIV antigens in a human physiological fluid test sample containing cells and which sample may have circulating antigen, said assay comprising:

(a) introducing into contact with a solid surface to which is bound a known quantity of a monoclonal antibody capable of binding to a common epitope of the HIV core antigens p55, p24, p39 and p33 without binding to the HIV core antigen p18 or HIV envelope antigens, a predetermined volume of the test sample and a known quantity of a lysing reagent for uniformly releasing antigens available from said cells during incubation;

(b) incubating said test sample and lysing reagent in contact with said surface to form resultant antigen-antibody complexes; and (c) incubating the resultant complexes and subjecting same to a labelled human anti-HIV antibody conjugate which is capable of producing a quantitatively measurable signal at picogram sensitivity of at least approximately 7.8 picograms per milliliter of test sample correlated to the signal for a normal negative test sample to indicate either antigen positive or negative for the test sample within a period of approximately four hours from the time of commencement of the immunoassay.

10. The immunoassay of claim 9 in which said human anti-HIV antibody conjugate of step (c) is labelled with an enzyme capable of producing said signal when contacted with an enzyme substrate.

11. The immunoassay of claim 9 in which said monoclonal antibody has the binding specificity characteristics of the monoclonal antibody produced by the hybridoma cell line on deposit with the American Type Culture Collection, Rockville, Md., A.T.C.C. deposit No. HB 9585.

12. The immunoassay of claim 9 in which said conjugate is a biotinylated antibody.

* * * * *